US00PP11908P2

(12) United States Plant Patent
Fuess

(10) Patent No.: US PP11,908 P2
(45) Date of Patent: Jun. 5, 2001

(54) CHRYSANTHEMUM PLANT NAMED 'EMPIRE SWEET DREAMS'

(76) Inventor: Janet S. Fuess, 22 Country Club Dr., New York Mills, NY (US) 13417

( * ) Notice: Subject to any disclaimer, the term of this patent is extended or adjusted under 35 U.S.C. 154(b) by 0 days.

(21) Appl. No.: 09/224,735

(22) Filed: Jan. 4, 1999

(51) Int. Cl.[7] ..... A01H 5/00
(52) U.S. Cl. ..... Plt./286
(58) Field of Search ..... Plt./286, 297

(56) References Cited

PUBLICATIONS

UPOV–ROM, 2000/02, Plant Variety Database, GTI Jouve Retrieval Software, citation for 'Empire Sweet Dreams'.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Empire Sweet Dreams', characterized by its uniformly mounded plant habit; large daisy-type inflorescences that are about 7 cm in diameter; attractive coral pink ray florets and bright yellow disc florets; and numerous inflorescences per plant.

1 Drawing Sheet

BACKGROUND OF THE INVENTION

The present invention relates to a new and distinct cultivar of Chrysanthemum plant, botanically known as *Dendranthema grandiflora* and referred to by the cultivar name Empire Sweet Dreams.

The new cultivar is a product of a planned breeding program conducted by the Inventor in New York Mills, N.Y. The objective of the breeding program is to create new garden-type Chrysanthemum cultivars having inflorescences with desirable inflorescence forms and floret colors and good garden performance.

The new cultivar originated from a cross made by the Inventor in October, 1992 of two unidentified proprietary seedling selections.

The cultivar Empire Sweet Dreams was discovered and selected by the Inventor as a flowering plant within the progeny of the stated cross in a controlled environment in New York Mills, N.Y., in August, 1993. The selection of this plant was based on its desirable inflorescence form and ray floret color.

Asexual reproduction of the new cultivar by terminal cuttings taken in a controlled environment in New York Mills, N.Y., has shown that the unique features of this new Chrysanthemum are stable and reproduced true to type in successive generations.

SUMMARY OF THE INVENTION

The cultivar Empire Sweet Dreams has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Empire Sweet Dreams'. These characteristics in combination distinguish 'Empire Sweet Dreams' as a new and distinct cultivar:

1. Uniformly mounded plant habit.
2. Glossy dark green leaves.
3. Large daisy-type inflorescences that are about 7 cm in diameter.

4. Attractive coral pink ray florets and bright yellow disc florets.
5. Numerous inflorescences per plant.

The new Chrysanthemum is similar to the Chrysanthemum cultivar Sandy (disclosed in U.S. Plant Pat. No. 7,531). However in side-by-side comparisons under commercial practice, plants of the new Chrysanthemum differed from plants of the cultivar Sandy in the following characteristics:

1. Plants of the new Chrysanthemum are shorter than plants of the cultivar Sandy.
2. Plants of the new Chrysanthemum have larger inflorescences than plants of the cultivar Sandy.
3. Ray florets of plants of the new Chrysanthemum are coral pink in color whereas ray florets of plants of the cultivar Sandy are golden bronze in color.

BRIEF DESCRIPTION OF THE PHOTOGRAPHS

The accompanying photographs illustrate the overall appearance of the new cultivar.

The photograph at the top of the sheet comprises a side perspective view of a typical flowering plant of 'Empire Sweet Dreams'.

The photograph at the bottom of the sheet comprises a close-up view of typical inflorescences of the cultivar 'Empire Sweet Dreams'. These photographs show the colors as true as it is reasonably possible to obtain in colored reproductions of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Leamington, Ontario, Canada, under conditions which approximate those generally used in commercial garden Chrysanthemum production. One rooted cutting was planted in a 15-cm container on Jul. 20, 1998 and plants were grown outdoors under natural season conditions. Measurements and numerical values represent averages for typical flowering containers.

Botanical classification: *Dendranthema grandiflora* cultivar Empire Sweet Dreams.

Commercial classification: Daisy-type garden chrysanthemum.

Parentage:

*Female or seed parent.*—Unidentified proprietary seedling selection.

*Male or pollen parent.*—Unidentified proprietary seedling selection.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous daisy-type garden Chrysanthemum. Inverted triangle. Stems initially upright, then outwardly spreading giving a uniformly mounded appearance to the plant. Freely branching with lateral branches potentially developing at every node, when pinched, about 10 laterals develop.

*Plant height.*—About 28 cm.

*Plant spread.*—About 43 cm.

*Foliage description.*—Leaf arrangement: Alternate. Length: About 5.4 cm. Width: About 5.2 cm. Apex: Cuspidate to mucronate. Base: Truncate. Margin: Palmately lobed, sinuses parallel to divergent. Texture: Upper surface sparsely pubescent; lower surface moderately pubescent. Veins prominent on lower surface. Petiole length: About 2.3 cm. Petiole diameter: About 3 mm. Color: Young foliage upper surface: Darker than 147A. Young foliage lower surface: Darker than 147B. Mature foliage upper surface: 147A, glossy. Mature foliage lower surface: Close to 147B. Venation upper surface: 147A. Venation lower surface: 147B.

Inflorescence description:

*Appearance.*—Daisy-type inflorescence form with oblong to elongated spoon-shaped ray florets. Inflorescences borne on terminals above foliage, arising from leaf axils. Disk and ray florets arranged acropetally on a capitulum. One inflorescence per terminal with numerous inflorescences per plant, about 9 per lateral stem.

*Flowering response.*—Under natural season conditions, plants flower in late September in the Northern Hemisphere, about 76 days after planting, and flower for at least three weeks depending on weather conditions.

*Inflorescence bud* (*before showing color*).—Height: About 5 mm. Diameter: About 8 mm. Phyllary color: Greener than 147A.

*Inflorescence size.*—Diameter: About 7 cm. Depth (height): About 1.3 cm. Diameter of disc: About 1.8 cm.

*Ray florets.*—Shape: Oblong to elongated spoon. Length: About 3.75 cm. Width: About 8.5 mm. Apex: Usually dentate. Margin: Entire. Texture: Smooth, glabrous, satiny. Orientation: Initially upright, then horizontal. Number of ray florets per inflorescence: About 67. Color: When opening: Upper surface: Close to 48A to 48C; iridescent. Lower surface: 27B to 27C. Opened inflorescence: Upper surface: 48C to 48D to 49A to 49C to 27A to 27B sometimes with pinkish, 49B to 49C, tones; iridescent. Lower surface: 27B to 27D.

*Disc florets.*—Shape: Tubular, apex dentate. Length: About 7 mm. Width: Apex: About 2 mm. Base: About 1 mm. Number of disc florets per inflorescence: Typically more than 150. Color: Immature: 154A. Mature: Apex: 12A. Mid-section: Greenish white. Base: White.

*Peduncle.*—Aspect: Flexible, angled about 45° to the stem. Length: First peduncle: About 6.5 cm. Fourth peduncle: About 7.8 cm. Diameter: About 2.5 mm. Texture: Pubescent. Color: Close to 147A.

*Reproductive organs.*—Androecium: Present on disc florets only. Anther color: 12A. Pollen: Scarce. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Empire Sweet Dreams', as illustrated and described.

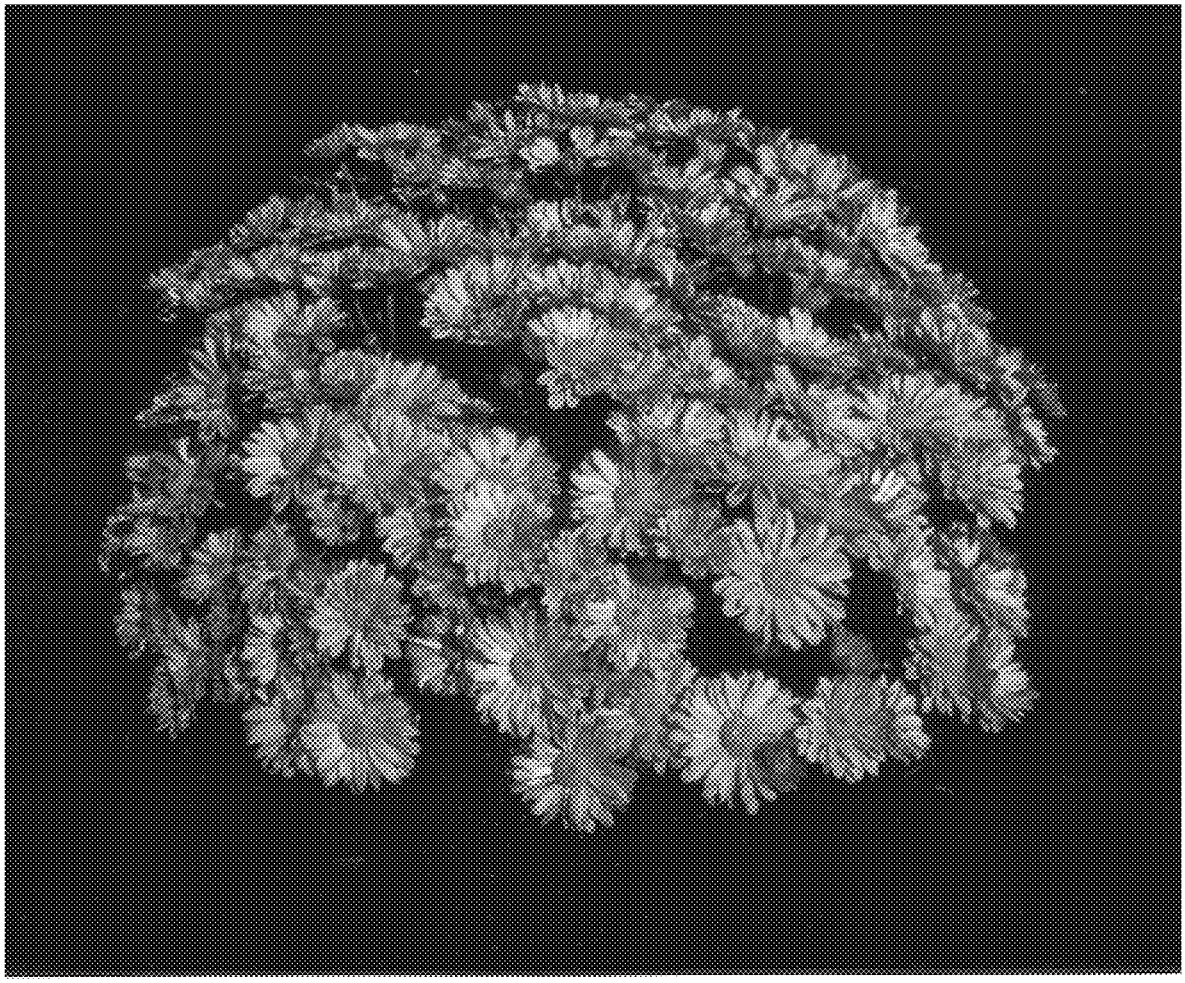
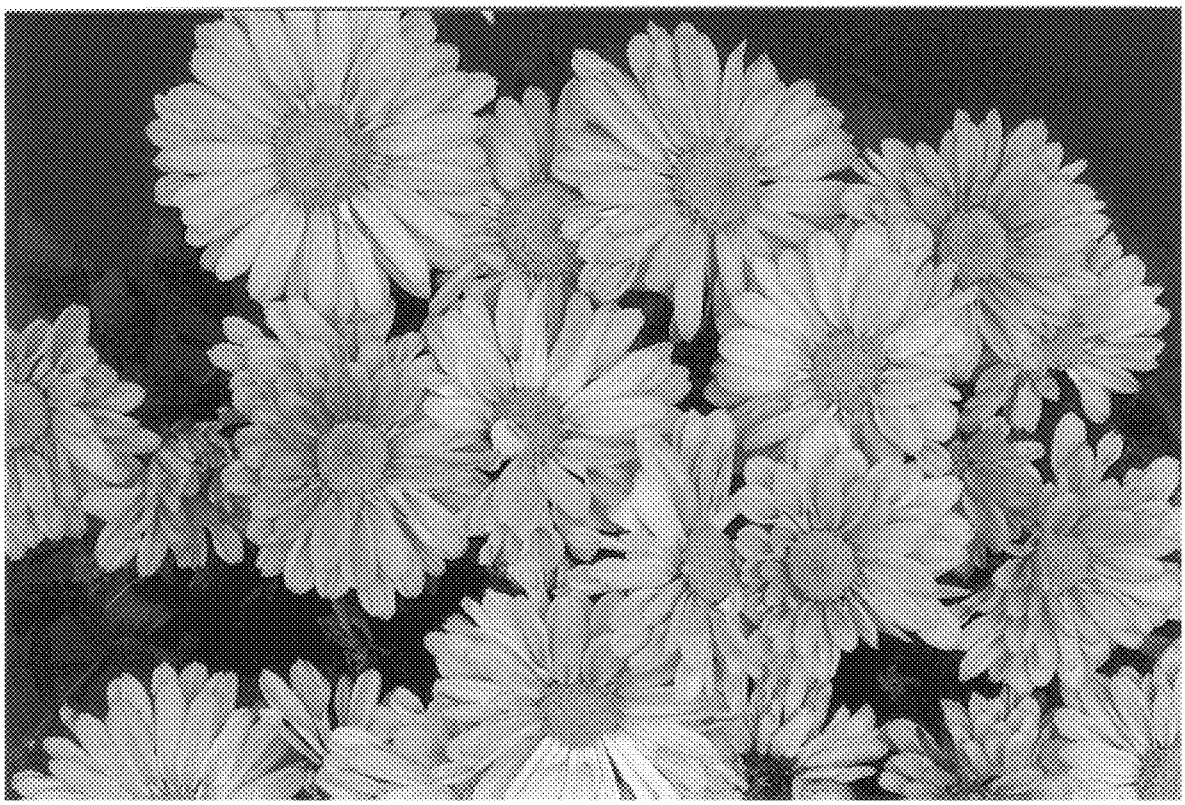

* * * * *